United States Patent [19]

Kurono et al.

[11] Patent Number: 4,868,189
[45] Date of Patent: Sep. 19, 1989

[54] URACIL DERIVATIVES FOR USE AS ANTI-TUMOR AGENTS HAVING SILICON CONTAINING SIDE CHAINS

[75] Inventors: Masayasu Kurono; Ryoichi Unno; Hiromoto Kimura; Hiroshi Ozawa; Takahiko Mitani; Takahito Jomori; Masahiko Koketsu; Hisashi Michishita; Kiichi Sawai, all of Nagoya, Japan

[73] Assignee: Sanwa Kagaku Kenkyusho Co., Nagoya, Japan

[21] Appl. No.: 140,503

[22] Filed: Jan. 4, 1988

[30] Foreign Application Priority Data

Jan. 5, 1987 [JP] Japan .......................... 62-17

[51] Int. Cl.$^4$ ............ A61K 31/505; C07F 7/10; C07D 239/54
[52] U.S. Cl. ....................... 514/274; 544/229; 544/302
[58] Field of Search ............ 544/229; 514/274

[56] References Cited

U.S. PATENT DOCUMENTS 4,560,679 12/1985 Toyoshima et al. ............ 549/4
4,778,797 10/1988 Toyoshima et al. ............ 544/229

FOREIGN PATENT DOCUMENTS

| 186452 | 7/1986 | European Pat. Off. . |
| 59-98091 | 6/1984 | Japan . |
| 122430 | 7/1984 | Japan .................. 544/229 |
| 61-65890 | 4/1986 | Japan . |
| 155390 | 7/1986 | Japan . |
| 62-10094 | 1/1987 | Japan . |
| 209112 | 9/1987 | Japan . |
| 226988 | 10/1987 | Japan .................. 544/229 |

OTHER PUBLICATIONS

Voronkov, Top Curr. Chem., vol. 84, pp. 77–135, (1979).
Abstract for JP 59/98091, (6/1984).
Abstract for JP 61/65890, (4/1986).
Abstract for JP 62/10094, (1/1987).
Tatsuro et al., Chemical Abstracts, vol. 108, No. 173534, (1988).
Masatoshi et al., Chemical Abstracts, vol. 109, No. 73646, (1988).

*Primary Examiner*—Mukund J. Shah
*Assistant Examiner*—E. Bernhardt
*Attorney, Agent, or Firm*—Armstrong, Nikaido, Marmelstein, Kubovcik & Murray

[57] ABSTRACT

An organo-silicone compound of the formula

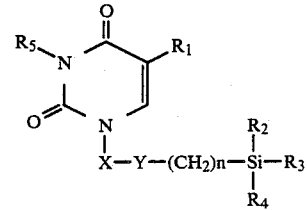

wherein X is a methylene or carbonyl radical, Y is an NH or O, n is an integer, $R_1$ is a hydrogen atom, halogen atom or alkyl group, $R_2$, $R_3$ and $R_4$ are an alkyl group, alkoxy group, phenyl radical or substituted phenyl radical, respectively, and $R_5$ is a hydrogen atom or a group of

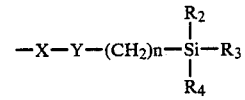

in which X, Y, n, $R_2$, $R_3$ and $R_4$ have the meanings as referred to, and used as an anti-tumor agent or for use in anti-tumor compositions.

13 Claims, No Drawings

URACIL DERIVATIVES FOR USE AS ANTI-TUMOR AGENTS HAVING SILICON CONTAINING SIDE CHAINS

BACKGROUND OF THE INVENTION

1. Field of the Invention

The present invention relates to novel organo-silicone compounds, a process for the preparation thereof, and an anti-tumor composition containing the compound as an effective ingredient therefor.

2. Related Arts

As organo-silicone compounds having anti-tumor activity, silatrane compounds have been known but their toxicity prohibits the use of such compounds for therapeutical purposes ["Top Curr. Chem." Vol. 84, page 77–135 (1979)].

5-fluorouracil (5-FU), Tegafur and Carmofur may be listed as examples of organo-silicone compounds which have been actually or clinically employed for curing tumors.

Among clinically employed compounds, 5-FU exhibits excellent anti-tumor activity but orally administered shows a high toxicity in that it often causes certain trouble in digestive canals, and thus this compound has exclusively been administered by injection. Tegafur shows a lower toxicity in oral dosage, but has a disadvantage in that its anti-tumor activity is low. Carmofur has a disadvantage in that side effects will appear in the central nervous system, and fevers and pollakiurea develop.

The present inventors have also studied and investigated various other organo-silicone compounds, for anti-tumor activities. The inventors reported that amine derivatives containing a silicon atom (U.S. Pat. No. 4,560,679 and Jap. Unexamined Pat. Appln. Gazette No. 155390/1986), and carbamoyl derivatives containing a silicon atom are effective anti-tumor compounds (Jap. Unexamined Pat. Appln. Gazette Nos. 98091/1984, 65890/1986 and 10094/1987).

These organo-silicone compounds reported by the inventors are effective as anti-tumor agents and exhibit a relatively low toxicity. However, a need exists to develop compounds exhibiting a greater efficiency.

SUMMARY OF THE INVENTION

In view of the above, the inventors have continued their study and investigations to discover more effective compounds having a higher anti-tumor activity and which show little or no toxicity, and which characteristics will not dictate the form of administration.

One of the objects of the invention, therefore, lies in providing such compounds.

Another object of the invention is to provide a process for the preparation of such compounds.

Other object of the invention is to provide an anti-tumor composition containing as an effective ingredient, at least one of such compounds.

According to the invention, the first or main object of the invention is attained by an organo-silicone compound of the formula

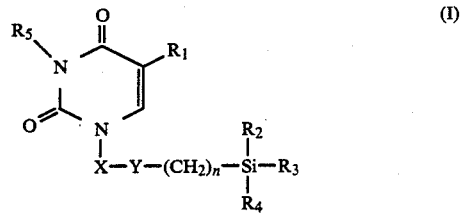

wherein X is a methylene or carbonyl radical, Y is NH or O, n is an integer of 3 to 7, $R_1$ is a hydrogen atom, halogen atom or alkyl group, $R_2$, $R_3$ and $R_4$ are an alkyl group, alkoxy group, phenyl radical or substituted phenyl radical, respectively, and $R_5$ is a hydrogen atom or a group of

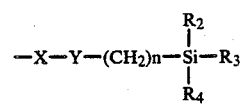

in which X, Y, n, $R_2$, $R_3$ and $R_4$ have the meanings as referred to above.

In connection with the compounds (I), the definition of each substituent shall be given as follows. The halogen may be fluorine, chlorine, bromine or iodine but fluorine is preferable. The alkyl group may be straight-chain alkyl radicals, branched-chain alkyl radicals or cycloalkyl radicals. As the straight-chain alkyl radicals, one having 1 to 10 carbon atoms, for instance methyl, ethyl, n-propyl, n-butyl, n-pentyl, n-hexyl, n-heptyl, n-decyl and the like may be listed. As the branched-chain alkyl radicals, isopropyl, isobutyl, s-butyl, t-butyl, isopentyl and the like may be listed. As the cycloalkyl radicals, cyclopropyl, cyclobutyl, cyclopentyl, cyclohexyl and the like may be listed. As the alkoxy group, methoxy, ethoxy, 2-methoxyethoxy and the like may be listed. As the substituent for phenyl radical, p-chloro, p-bromo, p-methyl, p-methoxy or the like may be listed.

According to the process for the invention, the compounds shown by said Formula (I) can be prepared by reacting a compound of the formula

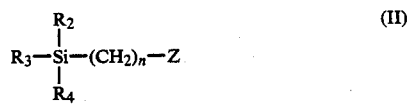

wherein $R_2$, $R_3$, $R_4$ and n have the meanings as referred to above, and Z is the radical $-NH_2$, $-N=C=O$ or $-OCH_2Cl$, with a compound of the formula

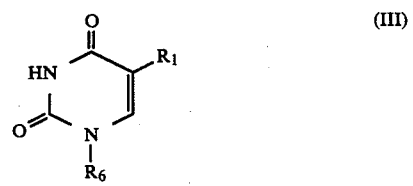

wherein $R_1$ has the meaning as referred to, and $R_6$ is a hydrogen atom, alkali metal or a radical of $-COCl$.

Referring to the process in more detail, there are following three synthetic routes.

Route A

According to this route, a silylalkylamine of the formula

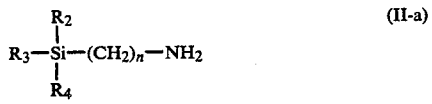

(II-a)

wherein $R_2$, $R_3$, $R_4$ and n have the meanings referred to above, is reacted with a 1-chloroformyl-5-substituted uracil of the formula

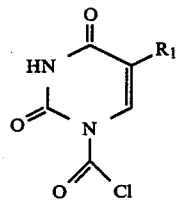

(III-a)

wherein $R_1$ has the meaning as referred to.

This reaction proceeds only by stirring the two raw materials in equi-molar amount, in the presence of a solvent. As the solvent, pyridine, N,N-dimethylformamide, dimethylsulfoxide, hexamethylphosphoryltriamide or the like may be employed. The reaction temperature depends upon the raw materials and kind of the solvent, but a temperature range of 0° to 10° C. is preferable, since the 1-chloroformyl-5-substituted uracil as one of the raw materials is, in general, not so stable. The 1-chloroformyl-5-substituted uracil can be prepared in accordance with the method as disclosed in "Bull. Chem.Soc. Japan" Vol. 50, pages 2406–2412 (1977). Trimethylsilylalkylamines can be prepared from trimethylsilylalkylalcohols, which are synthetheisized in accordance with the method as disclosed in "J. Amer. Chem." Vol. 74, page 1003 (1952), by a conversion into trimethylsilylalkylhalides with a suitable halogenating reagent, followed by the Gabriel synthesis or reduction of nitrides derived from the halides.

Route B

According to this route, an isocyanate of the formula

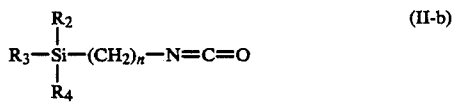

(II-b)

wherein $R_2$, $R_3$, $R_4$ and n have the meanings as referred to above, is reacted with a 5-substituted uracil of the formula

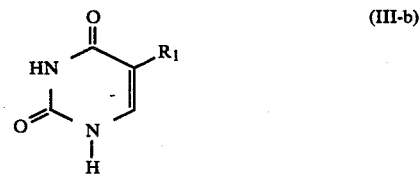

(III-b)

wherein $R_1$ has the meaning as referred to.

This reaction proceeds also by only stirring the two raw materials in equi-molar amount, in the presence of a solvent. As the solvent, those as described for Route A can be employed. The reaction temperature depends on the raw materials and kind of the solvent, but a range of 0° to 100° C. is genrally selected.

The isocyanate shown by the formula II-b can be prepared by reacting the compound of the formula II-a with phosgene in a molar amount of 1.0 to 3.0 times.

Route C

According to this route, a compound of the formula

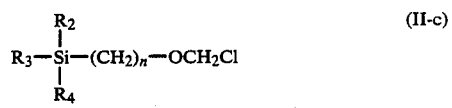

(II-c)

wherein $R_2$, $R_3$, $R_4$ and n have the meanings as referred to above, is reacted with a compound of the formula

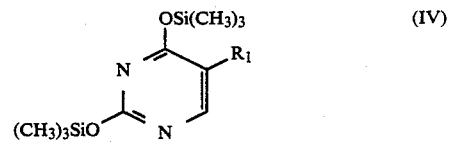

(IV)

wherein $R_1$ has the meaning as referred to.

The reaction will proceed only by stirring the raw materials, in the presence of a solvent, when the compound II-c is employed in molar amount of 1 to 2 times to the other raw material, but it can be accelerated by adding sodium iodide or a Lewis acid (boron trifluoride, titanium tetrachloride, tin tetrachloride or the like) in catalytic amount. As the solvent, acetonitrile, dichloromethane, chloroform or the like can be employed. The reaction temperature depends upon the raw materials and kind of the solvent but a range of 0° to 40° C. is preferably selected.

The α-chloroether shown by formula II-c can be prepared in accordance with a known method as disclosed in "Chem. Rev." Vol. 55, page 301 (1955). While, the compound shown by the formula IV has been known or can be prepared in accordance with the method as disclosed in BP 1168391.

Preparing an anti-tumor composition having at least one of the organo-silicone compounds, as effective ingredient(s), there is no limitation regarding to medicinal form and thus it may be made into an oral or non-oral administered composition. As for oral administration, tablet, capsule, granule, powder and the like may be listed. For non-oral administration, a suppository is exemplary listed. In connection with this, the medicine can be prepared by conventional processes. An amount for administrating the compound for human depends on kind of the compound selected, conditions of illness, age of a patient, form of the medicine and other factors but in general doses for an adult range between 300 to 5000 mg/day for oral administration, or 100 to 2000 mg/day in suppository form is preferable.

DETAILED DESCRIPTION OF THE PREFERRED EMBODIMENTS

The invention will now be further explained with reference to Examples for preparing the compounds according to the invention, Pharmacological Test Example as well as Examples for preparing medicines.

Example 1

1-[3-(trimethylsilyl)propylcarbamoyl]-5-fluorouracil (Compound 1)

To 13.0 g (0.100 mol) of 5-fluorouracil in 400 ml of anhydrous pyridine was added dropwise 9.90 g (50.0 mmol) of trimethylchloroformate with cooling on an ice-bath at 5° C. The mixture was stirred for 1 hour at 5° C. and then unreacted phosgene was removed in vacuo. To the reaction mixture was added dropwise 6.57 g (50.0 mmol) of 3-(trimethylsilyl)propylamine and the mixture was stirred for 1 hour at 5° to 10° C. and then the solvent was evaporated in vacuo. The resulting residue was dissolved in 300 ml of chloroform and 300 ml of 3% hydrochloric acid and the chloroform layer was washed with water, dried over sodium sulfate and concentrated in vacuo. The resulting crude crystals was recrystallized with ether to obtain 13.0 g of the desired compound (Yield: 90.4%).

Melting point: 146°–149° C.

Elementary analysis: $C_{11}H_{18}FN_3O_3Si$. Cal.: H 6.31; C 45.98; N 14.62. Found: H 6.41; C 46.14; N 14.77.

IR spectrum ($\nu_{max}^{KBr}$) cm$^{-1}$: 3300, 3200, 3100 ($\nu_{NH}$), 3050, 2960, 2830 ($\nu_{OH}$), 1765, 1730, 1690 ($\nu_{c=o}$), 1535 ($\delta_{NH}$), 1250 ($\nu_{c-si}$)

NMR spectrum (CDCl$_3$) δppm: −0.01 (9H, s, —SiMe$_3$) 0.3–0.7 (2H, m, —CH$_2$—Si—Me$_3$) 1.3–1.9 (2H, m, —CH$_2$CH$_2$SiMe$_3$) 3.2–3.6 (2H, m, —NHCH$_2$—) 8.59 (1H, s, J=7.0 Hz, C$_6$—H) 8.9–9.4 (1H, br., —CONH—).

MS spectrum (EI/DI) m/z: 272 (M$^+$-Me), 100 (base peak).

Example 2

1-[4-(trimethylsilyl)butylcarbamoyl]-5-fluorouracil (Compound 2)

The procedure described in Example 1 was repeated except that 7.25 g (50.0 mmol) of 4-(trimethylsilyl)butylamine was employed in place of 3-(trimethylsilyl)propylamine, to obtain 13.4 g of the desired compound (Yield: 89.2%).

Melting point: 129°–132° C.

Elementary analysis: $C_{12}H_{20}FN_3O_3Si$. Cal.: H 6.69; C 47.82; N 13.94. Found: H 6.83; C 47.62; N 13.91.

IR spectrum ($\nu_{max}^{kBr}$) cm$^{-1}$: 3330, 3200, 3090 ($\nu_{NH}$), 2970, 2950 ($\nu_{CH}$), 1740, 1670 ($\nu_{c=o}$), 1510 ($\delta_{NH}$), 1250 ($\nu_{c-si}$).

NMR spectrum (CDCl$_3$) δppm: −0.03 (9H, s, —SiMe$_3$) 0.3–0.7 (2H, m, —CH$_2$SiMe$_3$) 1.1–1.9 (4H, m, —(CH$_2$)$_2$CH$_2$SiMe$_3$) 3.2–3.6 (2H, m, —NHCH$_2$—) 8.59 (1H, d, J=7.0 Hz, C$_6$—H) 8.9–9.3 (1H, br., —CONH—).

MS spectrum (EI/DI) m/z: 286 (M$^+$-Me), 100 (base peak)

Example 3

1-[5-(trimethylsilyl)pentylcarbamoyl]-5-fluorouracil (Compound 3)

The procedure described in Example 1 was repeated except that 7.95 g (50.0 mmol) of 5-(trimethylsilyl)pentylamine was employed in place of 3-(trimethylsilyl)propylamine, to obtain 13.7 g of the desired compound (Yield: 91.1%).

Melting point: 118°–119° C.

Elementary analysis: $C_{13}H_{22}FN_3O_3Si$. Cal.: H 7.03; C 49.50; N 13.32. Found: H 7.22; C 49.52; N 13.32.

IR spectrum ($\nu_{max}^{kBr}$) cm$^{-1}$: 3336, 3188 ($\nu_{NH}$), 1738, 1680 ($\nu_{c=o}$), 1503 ($\delta_{NH}$), 1250 ($\nu_{c-si}$).

NMR spectrum (CDCl$_3$) δppm: −0.12 (9H, s, —SiMe$_3$) 0.1–0.6 (2H, m, —CH$_2$SiMe$_3$) 0.9–1.7 (6H, m, —(CH$_2$)$_3$CH$_2$SiMe$_3$) 3.1–3.5 (2H, m, —NHCH$_2$—) 7.5–7.9 (1H, m, —CONH—) 8.48 (1H, d, J=7.0 Hz, C$_6$—H) 8.8–9.2 (1H, m, N$_3$—H).

Example 4

1-[7-(trimethylsilyl)heptylcarbamoyl]-5-fluorouracil (Compound 4)

The procedure described in Example 1 was repeated except that 9.35 g (50.0 mmol) of 7-(trimethylsilyl)heptylamine was employed in place of 3-(trimethylsilyl)propylamine, to obtain 15.5 g of the desired compound (Yield: 90.5%).

Melting point: 118°–119° C.

Elementary analysis: $C_{15}H_{26}FN_3O_3Si$. Cal.: H 7.63; C 52.45; N L12.23. Found: H 7.90; C 52.60; N 12.36.

IR spectrum ($\nu_{max}^{kBr}$) cm$^{-1}$: 3334, 3186 ($\nu_{NH}$), 1737, 1680 ($\nu_{c=o}$), 1503 ($\delta_{NH}$), 1250 ($\nu_{c-si}$).

NMR spectrum (CDCl$_3$) δppm: −0.17 (9H, s, —SiMe$_3$) 0.1–0.6 (2H, m, —CH$_2$SiMe$_3$) 1.1–1.5 (10H, m, —(CH$_2$)$_5$CH$_2$SiMe$_3$) 3.1–3.5 (2H, m, —NHCH$_2$—) 8.48 (1H, d, J=7.0 Hz, C$_6$—H) 8.9–9.1 (1H, m, —CONH—).

Example 5

1-[2-(trimethylsilyl)ethyloxymethyl]-5-fluorouracil (Compound 5a) and 1,3-bis[2-(trimethylsilyl)ethyloxymethyl]-5-flouorouracil (Compound 5b)

To a mixture of 2.74 g (10.0 mmol) of 2,4-bis(trimethylsilyl)-5-fluorouracil and 750 mg (5.00 mmol) of sodium iodide in 35.0 ml of anhydrous acetonitrile was added dropwise 2.50 g (15.0 mmol) of 2-(trimethylsilyl)ethyloxymethyl chloride to maintain a temperature of the solution at 20° C. After stirring the mixture for 10 minutes at 20° C., the solvent was evaporated in vacuo, and the resulting residue was dissolved in 100 ml of chloroform and 100 ml of water and the chloroform layer was dried over sodium sulfate and concentrated in vacuo. The resulting residue was crystallized with a small amount of n-hexane to obtain 1.12 g (43.1%) of the desired compound (5a).

While, the filtrate was concentrated and the resulting residue was purified by silica-gel chromatography (developing solvent: chloroform/methanol=300/1) to obtain an additional 0.39 g (15.0%) of the compound 5a as well as 1.44 g (36.9%) of the other desired compound (5b).

Compound 5a

Melting point: 132°–133° C.

Elementary analysis: $C_{10}H_{17}FN_2O_3Si$. Cal.: H 6.58; C 46.14; N 10.76. Found: H 6.74; C 46.42; N 10.87.

IR spectrum ($\nu_{max}^{kBr}$) cm$^{-1}$: 1715, 1690, 1660 ($\nu_{c=o}$), 1250 ($\nu_{c-si}$), 1090 ($\nu_{c-o}$).

NMR spectrum (CDCl$_3$) δppm: −0.11 (9H, s, —SiMe$_3$) 0.85 (2H, t, J=8.0 Hz, —CH$_2$SiMe$_3$) 0.58 (2H, t, J=8.0 Hz, —OCH$_2$CH$_2$—) 5.10 (2H, s, —OCH$_2$N<) 7.39 (1H, d, J=5.0 Hz, C$_6$—H) 9.83 (1H, br., —NH—).

Mass spectrum (EI/DI) m/z: 260 (M$^+$), 187 (base peak)

Compound 5b

IR spectrum ($\nu_{max}^{kBr}$) cm$^{-1}$: 1725, 1690, 1670 ($\nu_{c=o}$), 1250 ($\nu_{c-si}$), 1090 ($\nu_{c-o}$).

NMR spectrum (CDCl$_3$) δppm: −0.10 (18H, s, —SiMe$_3$×2) 0.84 (4H, t, J=8.0 Hz, —CH$_2$SiMe$_3$×2)

3.4–3.8 (4H, m, —OCH$_2$CH$_2$—×2) 5.10 (2H, s, —OCH$_2$N<) 5.37 (2H, s, —OCH$_2$N<) 7.36 (1H, d, J=5.0 Hz, C$_6$—H).

MS spectrum (EI/DI) m/z: 375 (M-Me), 73 (base peak).

High MS spectrum (m/z): 375.1584 (M-Me, C$_{15}$H$_{28}$FN$_2$O$_4$Si$_2$; Cal. 375.1571).

Example 8

1-[3-(trimethylsilyl)propyloxymethyl]-5-fluorouracil (Compound 6a) and
1.3-bis[3-(trimethylsilyl)propyloxymethyl]-5-fluorouracil (Compound 6b)

The procedure described in Example 5 was repeated except that 2.73 g (15.0 mmol) of 3-(trimethylsilyl)-propyloxymethyl chloride was employed in place of 2-(trimethylsilyl)ethoxyloxymethyl chloride, to obtain 1.70 g (61.7%) and 0.82 g (19.5%) of the desired compounds 6a and 6b, respectively.

Compound 6a

Melting point: 119°–120° C. Elementary analysis: C$_{11}$H$_{19}$FN$_2$O$_3$Si. Cal.: H 6.98; C 48.15; N 10.21. Found: H 7.24; C 47.98; N 10.16.

IR spectrum ($\nu_{max}^{kBr}$) cm$^{-1}$: 1700, 1660 ($\nu_{c=o}$), 1250 ($\nu_{c-si}$).

NMR spectrum (CDCl$_3$) δppm: −0.17 (9H, s, —SiMe$_3$) 0.2–0.5 (2H, m, —CH$_2$SiMe$_3$) 1.2–1.8 (2H, m, —CH$_2$CH$_2$SiMe$_3$) 3.39 (2H, t, J=7.0 Hz, —CH$_2$C-H$_2$O—) 5.04 (2H, s, —OCH$_2$N<) 7.34 (1H, d, J=5.0 Hz, C$_6$—H) 9.75 (1H, br., —NH—).

MS spectrum (EI/DI) m/z: 260 (M-Me), 73 (base peak).

Compound 6b

IR spectrum ($\nu_{max}^{kBr}$) cm$^{-1}$: 1725, 1690, 1670 ($\nu_{c=o}$), 1250 ($\nu_{c-si}$).

NMR spectrum (CDCl$_3$) δppm: −0.10 (18H, s, —SiMe$_3$×2) 0.2–0.6 (4H, m, —CH$_2$SiMe$_3$×2) 1.2–1.8 (4H, m, —CH$_2$CH$_2$SiMe$_3$×2) 3.3–3.7 (4H, m, —CH$_2$C-H$_2$—×2) 5.13 (2H, s, —OCH$_2$N<) 5.41 (2H, s, —OCH$_2$N<) 7.36 (1H, d, J=5.0 Hz, C$_6$—H).

MS spectrum (EI/DI) m/z: 418 (M+), 403 (M-Me) 73 (base peak).

High MS spectrum (m/z): 418.2142 (M+, C$_{18}$H$_{35}$FN$_2$O$_4$Si$_2$; Cal. 418.2120).

Example 7

1-[5-(trimethylsilyl)pentyloxymethyl]-5-flourouracil (Compound 7a) and
1,3-bis[5-(trimethylsilyl)pentyloxymethyl]-5-fluorouracil (Compound 7b)

The procedure described in Example 5 was repeated except that 3.13 g (15.0 mmol) of 5-(trimethylsilyl)pentyloxymethyl chloride was employed in place of 2-(trimethylsilyl)ethyloxymethyl chloride, to obtain 2.22 g (73.4%) and 1.10 g (23.2%) of the desired compounds 7a and 7b, respectively.

Compound 7a

Melting point: 86°–87° C.

Elementary analysis: C$_{13}$H$_{23}$FN$_2$O$_3$Si. Cal.: H 7.67; C 51.63; N 9.26. Found: H 7.78; C 51.33; N 9.25.

IR spectrum ($\nu_{max}^{kBr}$) cm$^{-1}$: 1700, 1665 ($\nu_{c=o}$), 1250 ($\nu_{c-si}$).

NMR spectrum (CDCl$_3$) δppm: −0.14 (9H, s, —SiMe$_3$) 0.2–0.6 (2H, m, —CH$_2$SiMe$_3$) 1.0–1.7 (6H, m, —(CH$_2$)$_3$CH$_2$SiMe$_3$) 3.3–3.6 (2H, m, —OCH$_2$CH$_2$—) 5.11 (2H, s, —OCH$_2$N<) 7.39 (1H, d, J=5.0 Hz, C$_6$—H) 9.83 (1H, br., —NH—).

MS spectrum (EI/DI) m/z: 287 (M-Me), 73 (base peak).

Compound 7b

IR spectrum ($\nu_{max}^{kBr}$) cm$^{-1}$: 1730, 1670 ($\nu_{c=o}$), 1250 ($\nu_{c-si}$).

NMR spectrum (CDCl$_3$) δppm: −0.09 (18H, s, —SiMe$_3$×2) 0.2–0.6 (4H, m, —CH$_2$SiMe$_3$×2) 1.0–1.7 (12H, m, —(CH$_2$)$_3$CH$_2$SiMe$_3$×2) 3.3–3.8 (4H, m, —OCH$_2$C-H$_2$—×2) 5.12 (2H, s, —OCH$_2$N<) 5.39 (2H, s, —OCH$_2$N<) 7.35 (1H, d, J=5.0 Hz, C$_6$—H).

MS spectrum (CI/DI) m/z: 475 (M+ +1, base peak).

High MS spectrum (m/z): 474.2763 (M+, C$_{22}$H$_{43}$FN$_2$O$_4$Si$_2$; Cal. 474.2746).

Pharmacological Test Example 1

(Anti-tumor activity to Lewis lung carcinoma)

Under a skin of female BDF$_1$ strain mice (age of 6 weeks), Lewis lung carcinoma cells (2.5×10$^5$) were transplanted to form of a tumor. Each of testing compounds was orally administered to the animals 3 times (at 4th, 8th and 10th day after the transplantation, respectively) and then each animal was sacrificed at 17th day after the transplantation to measure the weight of the tumor.

An anti-tumor activity of each compound tested was calculated based on following equation, as an inhibition of tumor proliferation.

$$\text{Inhibition of proliferation (\%)} = \frac{C - T}{C} \times 100$$

wherein

T: Weight of tumor in the testing compound administered group, and

C: Weight of tumor in the control group not administered the testing compound.

The results are shown in following Table.

TABLE

| Compound | Dose/day × 3 (mg/kg) | Inhibition of proliferation (%) |
|---|---|---|
| 1 | 239 | 86 |
|   | 398 | 100 |
|   | 557 | 100 |
| 2 | 250 | 82 |
|   | 417 | 99 |
|   | 584 | 100 |
| 3 | 282 | 45 |
|   | 437 | 88 |
|   | 612 | 97 |
| 4 | 285 | 59 |
|   | 476 | 97 |
|   | 666 | 100 |

Pharmacological Test Example 2

(Acute toxicity)

Female ICR strain mice (age of 5 weeks) were used for this experiment. Compound 2 suspended in 1% Tween 80-0.5% CMC solution was given to each animal orally. General condition, behavior, body weight and mortality were observed daily throughout the experimental period of 14 days.

Then, a value of LD$_{50}$ was calculated in accordance with the Litchfield-Wilcoxon method and found to be 820 mg/kg.

Medicine Preparation Example 1 (Tablet)

Following ingredients were prescripted and combined in a conventional manner to prepare tablets.

| Compound 1 | 100 (mg) |
|---|---|
| Crystalline cellulose | 20 |
| Lactose | 41 |
| Corn starch | 30 |
| Hydroxypropylcellulose | 6 |
| Magnesium stearate | 3 |
| | 200 mg/tablet |

Medicine Preparation Example 2 (Capsule)

Following ingredients were prescripted and combined in a conventional manner to prepare capsules.

| Compound 2 | 200 (mg) |
|---|---|
| Crystalline cellulose | 50 |
| Silicic anhydride | 2 |
| Magnesium stearate | 3 |
| | 255 mg/capsule |

Medicine Preparation Example 3 (Granule)

Following ingredients were prescripted and combined in a conventional manner to prepare granules.

| Compound 3 | 500 (mg) |
|---|---|
| lactose | 323 |
| Corn starch | 150 |
| Polyvinylpyrrolidone | 25 |
| Silicic anhydride | 2 |
| | 1000 mg/package |

Medicine Preparation Example 4 (Suppository)

Following ingredients were prescripted and combined in a conventional manner to prepare suppositories.

| Compound 4 | 300 (mg) |
|---|---|
| Witep-Sol W-35 (Trademark) | 1700 |
| | 2000 mg/piece |

What is claimed is:

1. An organo-silicone compound of the formula

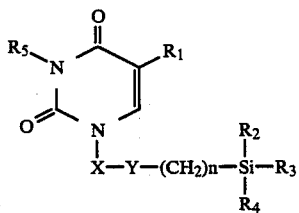

wherein X is a methylene or carbonyl radical, Y is an NH or O, n is an integer of 3 to 7, $R_1$ is a hydrogen atom, halogen atom or a $C_1$–$C_{10}$ straight or branched chain alkyl group, $R_2$, $R_3$ and $R_4$ are a $C_1$–$C_{10}$ straight or branched chain alkyl group, an alkoxy radical, selected from the group consisting of methoxy, ethoxy, and 2-methoxyethoxy, a phenyl radical or a p-bromo, p-chloro, p-methyl or p-methoxy substituted phenyl radical, respectively, and $R_5$ is a hydrogen atom or a group of

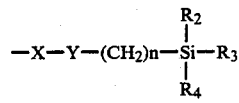

in which X, Y, n, $R_2$, $R_3$ and $R_4$ have the meanings above.

2. An organo-silicone compound as claimed in claim 1, wherein said compound is 1-[3-(trimethylsilyl)propylcarbamoyl]-5-fluorouracil.

3. An organo-silicon compound as claimed in claim 1, wherein said compound is 1-[4-(trimethylsilyl)butylcarbamoyl]-5-fluorouracil.

4. An organo-silicone compound as claimed in claim 1, wherein said compound is 1-[5-(trimethylsilyl)pentylcarbamoyl]-5-fluorouracil.

5. An organo-silicone compound as claimed in claim 1, wherein said compound is 1-[7-(trimethylsilyl)heptylcarbamoyl]-5-fluorouracil.

6. An organo-silicone compound as claimed in claim 1, wherein said compound is 1-[2-(trimethylsilyl)ethyloxymethyl]-5-fluorouracil.

7. An organo-silicone compound as claimed in claim 1, wherein said compound is 1-[3-(trimethylsilyl)propyloxymethyl]-5-fluorouracil.

8. An organo-silicone compound as claimed in claim 1, wherein said compound is 1-[5-(trimethylsilyl)pentyloxymethyl]-5-fluorouracil.

9. An organo-silicone compound as claimed in claim 1, wherein said compound is 1,3-bis[2-(trimethylsilyl)ethyloxymethyl]-5-fluorouracil.

10. An organo-silicone compound as claimed in claim 1, wherein said compound is 1,3-bis[3-(trimethylsilyl)propyloxymethyl]-5-fluorouracil.

11. An organo-silicone compound as claimed in claim 1, wherein said compound is 1,3-bis[5-(trimethylsilyl)pentyloxymethyl]-5-fluorouracil.

12. An anti-tumor composition comprising an effective amount of an organo-silicone compound of the formula

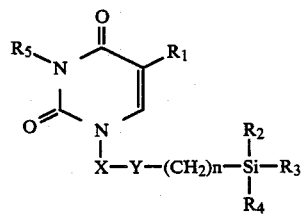

wherein X is a methylene or carbonyl radical, Y is an NH or O, n is an integer of 3 to 7, $R_1$ is a hydrogen atom, halogen atom or a $C_1$–$C_{10}$ straight or branched chain alkyl group, $R_2$, $R_3$ and $R_4$ are a $C_1$–$C_{10}$ straight or branched chain alkyl group, an alkoxy radical, selected from the group consisting of methoxy, ethoxy, and 2-methoxyethoxy, a phenyl radical or a p-bromo, p-chloro, p-methyl or p-methoxy substituted phenyl radical, respectively, and $R_5$ is a hydrogen atom or a group of

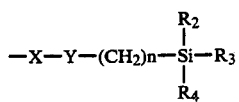

in which X, Y, n, $R_2$, $R_3$ and $R_4$ have the meanings as referred to above, and a pharmaceutically acceptable carrier.

13. An anti-tumor composition as claimed in claim 12, wherein said organo-silicone compound is at least one compound selected from the group consisting of
(a) 1-[3-(trimethylsilyl)propylcarbamoyl]-5-fluorouracil,
(b) 1-[4-(trimethylsilyl)butylcarbamoyl]-5-fluorouracil,
(c) 1-[5-(trimethylsilyl)pentylcarbamoyl]-5-fluorouracil,
(d) 1-[7-(trimethylsilyl)heptylcarbamoyl]-5-fluorouracil,
(e) 1-[2-(trimethylsilyl)ethyloxymethyl]-5-fluorouracil,
(f) 1-[3-(trimethylsilyl)propyloxymethyl]-5-fluorouracil,
(g) 1-[5-(trimethylsilyl)pentyloxymethyl]-5-fluorouracil,
(h) 1,3-bis[2-(trimethylsilyl)ethyloxymethyl]-5-fluorouracil,
(i) 1,3-bis[3-(trimethylsilyl)propyloxymethyl]-5-fluorouracil, and
(j) 1,3-bis[5-(trimethylsilyl)pentyloxymethyl]-5-fluorouracil.

* * * * *